(12) United States Patent
Choi et al.

(10) Patent No.: US 8,798,707 B2
(45) Date of Patent: Aug. 5, 2014

(54) FLEXIBLE, MULTI-CHANNEL MICROELECTRODE FOR RECORDING LABORATORY ANIMAL EEG AND METHOD FOR RECORDING LABORATORY ANIMAL EEG USING THE SAME

(75) Inventors: Ji Hyun Choi, Seongnam-si (KR); Hee Sup Shin, Euiwang-si (KR); Klaus Peter Koch, Darmstadt (DE)

(73) Assignee: Korea Institute of Science and Technology (KR)

( * ) Notice: Subject to any disclaimer, the term of this patent is extended or adjusted under 35 U.S.C. 154(b) by 222 days.

(21) Appl. No.: 13/123,217

(22) PCT Filed: Dec. 24, 2008

(86) PCT No.: PCT/KR2008/007671
§ 371 (c)(1),
(2), (4) Date: Jun. 1, 2011

(87) PCT Pub. No.: WO2010/041794
PCT Pub. Date: Apr. 15, 2010

(65) Prior Publication Data
US 2011/0224528 A1    Sep. 15, 2011

(30) Foreign Application Priority Data

Oct. 8, 2008    (KR) .......................... 10-2008-0098655

(51) Int. Cl.
*A61B 5/0478*    (2006.01)
(52) U.S. Cl.
CPC ........... *A61B 5/0478* (2013.01); *A61B 2503/40* (2013.01); *A61B 2562/046* (2013.01); *A61B 2562/0209* (2013.01)
USPC .......................................... 600/378; 607/116
(58) Field of Classification Search
CPC ..................... A61B 5/0478; A61B 2562/0209; A61B 2562/046
USPC ........................... 600/373, 377, 378; 607/116
See application file for complete search history.

(56) References Cited

U.S. PATENT DOCUMENTS

| 4,461,304 A * | 7/1984 | Kuperstein .................... 600/378 |
| 6,624,510 B1 * | 9/2003 | Chan et al. .................... 257/734 |

(Continued)

FOREIGN PATENT DOCUMENTS

| JP | 06-189919 | 7/1994 |
| JP | 3193471 | 5/2001 |

(Continued)

OTHER PUBLICATIONS

International Search Report issued Jul. 28, 2009 by Korean Intellectual Property Office re: Application No. PCT/KR2008/007671, citing JP 3193471B2, JP 06-189919A and KR 10-2002-0064283A.

(Continued)

*Primary Examiner* — Lee S Cohen
(74) *Attorney, Agent, or Firm* — Cantor Colburn LLP

(57) ABSTRACT

Disclosed are a novel, elastic, biocompatible, micro-sized, polyimide-based multi-channel microelectrode for recording of electroencephalography (EEG) from a laboratory animal including mouse, and a method for recording of laboratory animal EEG using the microelectrode. The microelectrode may include 2 grounding electrodes and 32 recording electrodes. A connector for signal transmission easily connects the microelectrode to a signal acquiring apparatus. The total weight of the microelectrode, including the connector, does not exceed 150 mg. Laboratory animal EEG, including that of mouse, provides the advantage of monitoring the brain state of a freely moving animal following a genetic or pharmaceutical manipulation. The microelectrode can be implanted without surgery and may be detached from wires while EEG is not recorded from the laboratory animal. The microelectrode can successfully acquire broadband EEG signals from the skull of the laboratory animal and is effective in monitoring spatial and temporal pattern of brain activities of the laboratory animal.

8 Claims, 11 Drawing Sheets

(56) References Cited

U.S. PATENT DOCUMENTS

| | | | |
|---|---|---|---|
| 6,829,498 B2* | 12/2004 | Kipke et al. | 600/378 |
| 6,973,342 B1* | 12/2005 | Swanson | 600/378 |
| 7,536,215 B2* | 5/2009 | Putz et al. | 600/378 |
| 7,937,160 B2* | 5/2011 | Garabedian et al. | 607/116 |
| 8,386,007 B2* | 2/2013 | Williams et al. | 600/378 |
| 2006/0135862 A1* | 6/2006 | Tootle et al. | 600/373 |
| 2006/0173263 A1* | 8/2006 | He et al. | 600/378 |
| 2008/0249391 A1* | 10/2008 | Moxon et al. | 600/373 |
| 2009/0177144 A1* | 7/2009 | Masmanidis et al. | 604/66 |

FOREIGN PATENT DOCUMENTS

| | | |
|---|---|---|
| KR | 10-2002-0064283 | 8/2002 |
| KR | 10-0466954 | 1/2005 |

OTHER PUBLICATIONS

Written Opinion issued Jul. 28, 2009 by Korean Intellectual Property Office re: Application No. PCT/KR2008/007671.

* cited by examiner

FLEXIBLE, MULTI-CHANNEL MICROELECTRODE FOR RECORDING LABORATORY ANIMAL EEG AND METHOD FOR RECORDING LABORATORY ANIMAL EEG USING THE SAME

TECHNICAL FIELD

Disclosed are a flexible, multi-channel microelectrode for recording of laboratory animal electroencephalography (EEG) and a method for recording of laboratory animal EEG using the microelectrode.

BACKGROUND ART

Genetically modified laboratory animals, particularly mice, are a powerful tool in the study of human diseases and treatments thereof. The benefit is extended to the field of neuroscience. Studies are ongoing on the function and behavior of the brain in molecular level, using genetically modified mice. Particularly, the recording of electroencephalography (EEG) of genetically modified mice is an important tool in understanding the mechanism of spontaneous oscillations of the brain or epilepsy in molecular or cellular level.

In the recording of EEG of most laboratory animals, including mice, integrated activities over the whole brain is monitored using one or two channels. The existing EEG electrode is in the form of micro sized screw connected to bare wires for signaling. The screw electrode is typically fixed to the brain passing through a hole made on the skull, and dental cement is applied on the skull for the purpose of fixation and shielding from external noise. The head size of most laboratory animals including mouse is too small to implant a plurality of screw electrodes. Further, since the mouse skull is relatively soft and about 200-730 μm thick, bleeding may occur easily during the surgical operation. Despite these limitations, EEG of laboratory animals, especially that of mice, has been an important tool for monitoring the neuronal and brain dynamics in vivo following a genetic or pharmaceutical manipulation.

DISCLOSURE

Technical Problem

This disclosure is directed to providing a method for effective recording of electroencephalography (EEG) using a polyimide-based microelectrode in a least invasive manner from as many sites as possible from a freely moving laboratory animal. The disclosure is also directed to monitoring brain activities and acquiring functional brain images by successfully collecting broadband EEG signals from the skull of a laboratory animal using the microelectrode.

Technical Solution

There is provided a multi-channel microelectrode for recording of laboratory animal electroencephalography (EEG) including a grounding electrode and 4 or more recording electrodes, each of which includes a conductive material formed on a polyimide substrate. In the microelectrode, the 4 or more recording electrodes are aligned in parallel lines extending from a centerline on both sides.

There is also provided a method for recording of laboratory animal EEG using the multi-channel microelectrode, including positioning the multi-channel microelectrode on the skull of a laboratory animal and acquiring broadband EEG from the skull of the laboratory animal.

Advantageous Effects

Electroencephalography (EEG) of free moving laboratory animals, particularly mice, enables monitoring of the brain in vivo following a genetic or pharmaceutical manipulation. The microelectrode according to an embodiment disclosed herein needs no surgical operation for implantation and, when EEG is not recorded, wires may be easily detached from the laboratory animal. The microelectrode is capable of successfully acquiring broadband EEG signals from the skull and is effective in monitoring the spatial and temporal pattern of brain activities. Through multi-channel EEG employing statistical and dynamical variables such as entropy, coherence and phase shift, it is possible to monitor the spatial and temporal pattern of the brain of a living laboratory animal, especially a mouse.

DESCRIPTION OF DRAWINGS

The above and other aspects, features and advantages of the disclosed exemplary embodiments will be more apparent from the following detailed description taken in conjunction with the accompanying drawings in which:

FIG. 11 shows tracing of randomly selected EEG signals under Avertin anesthesia. The dynamics of individual channels have relatively no coherence.

FIG. 12 shows EEG exhibiting seizure waves (continuous spike waves) 2 minutes after the administration of 4-aminopyridine (4-AP). The vertical broken line indicates phase shift time from periodic to biperiodic.

FIG. 13 shows EEG exhibiting focal spike-and-wave discharge (SWD) minutes after the administration).);

Figure 15:
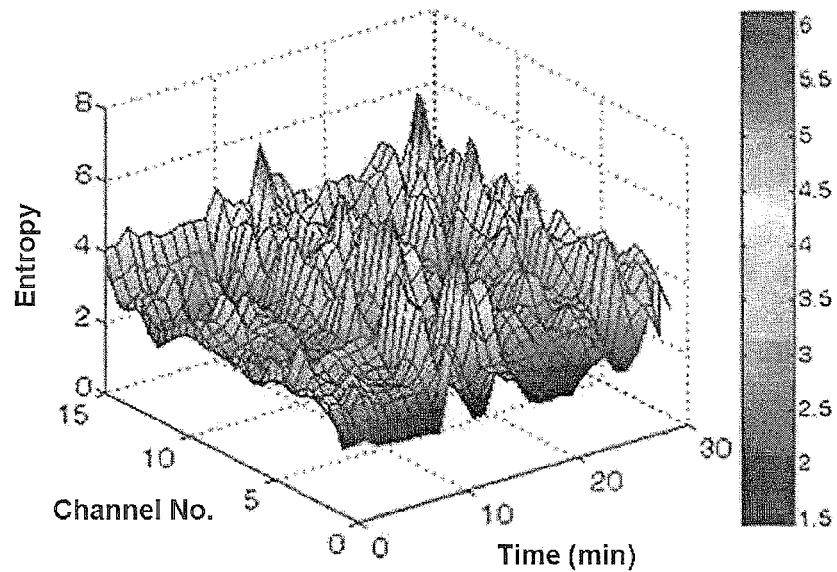
Figure 16:
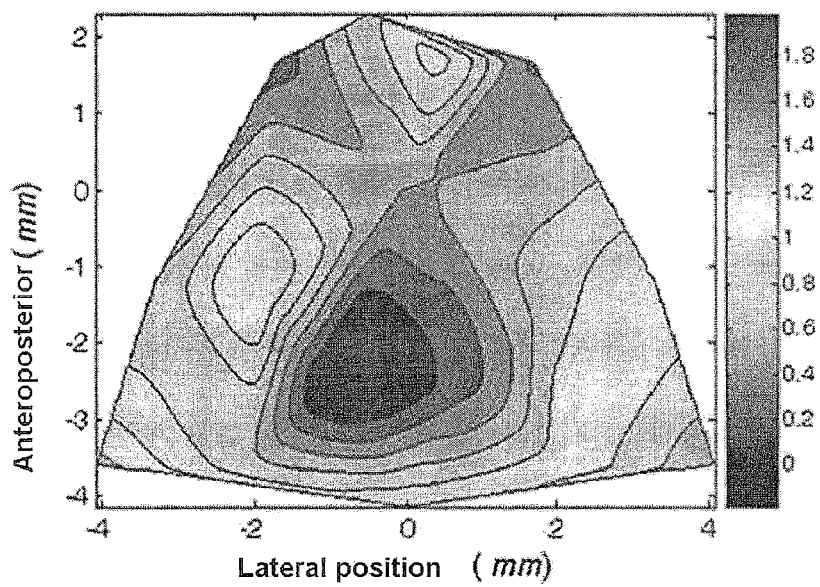
Figure 17:
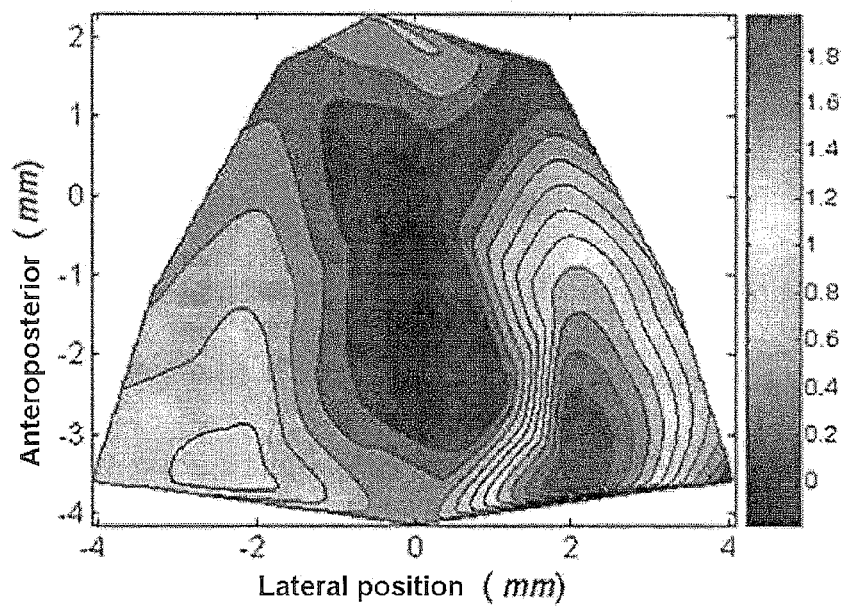
Figure 18:
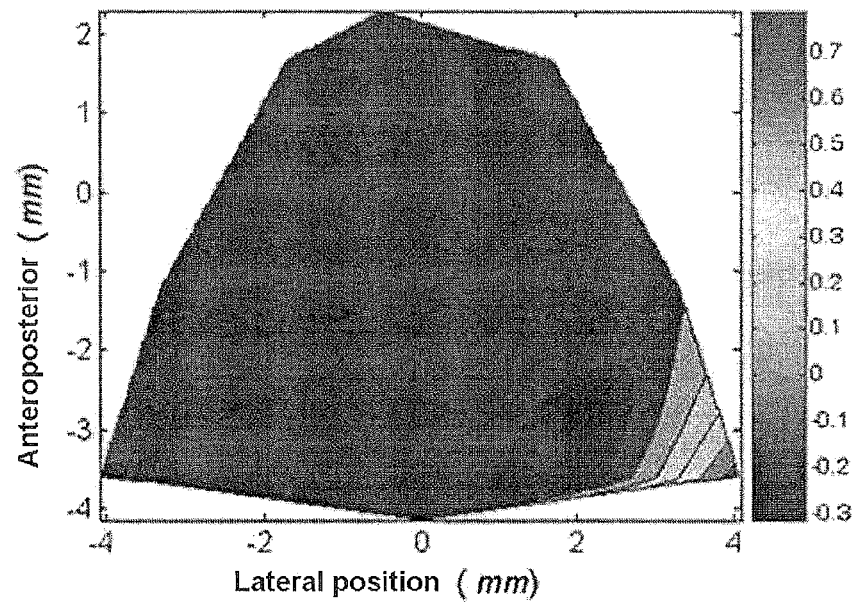
Figure 19:
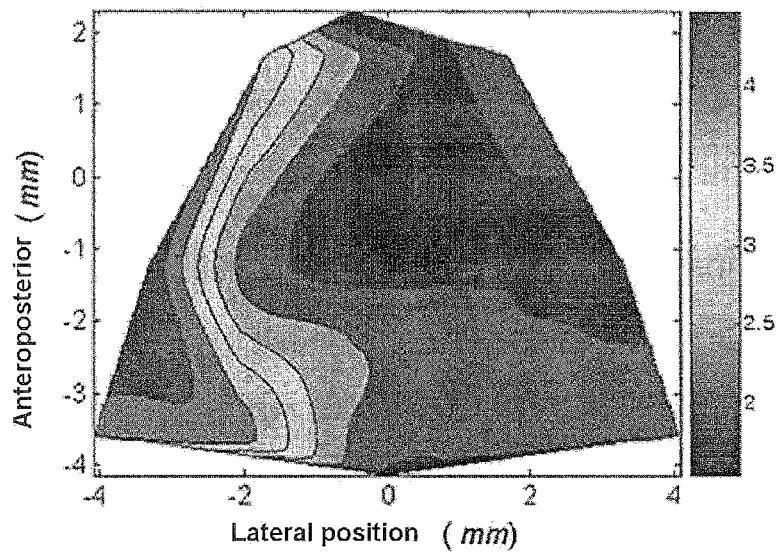
Figure 20:
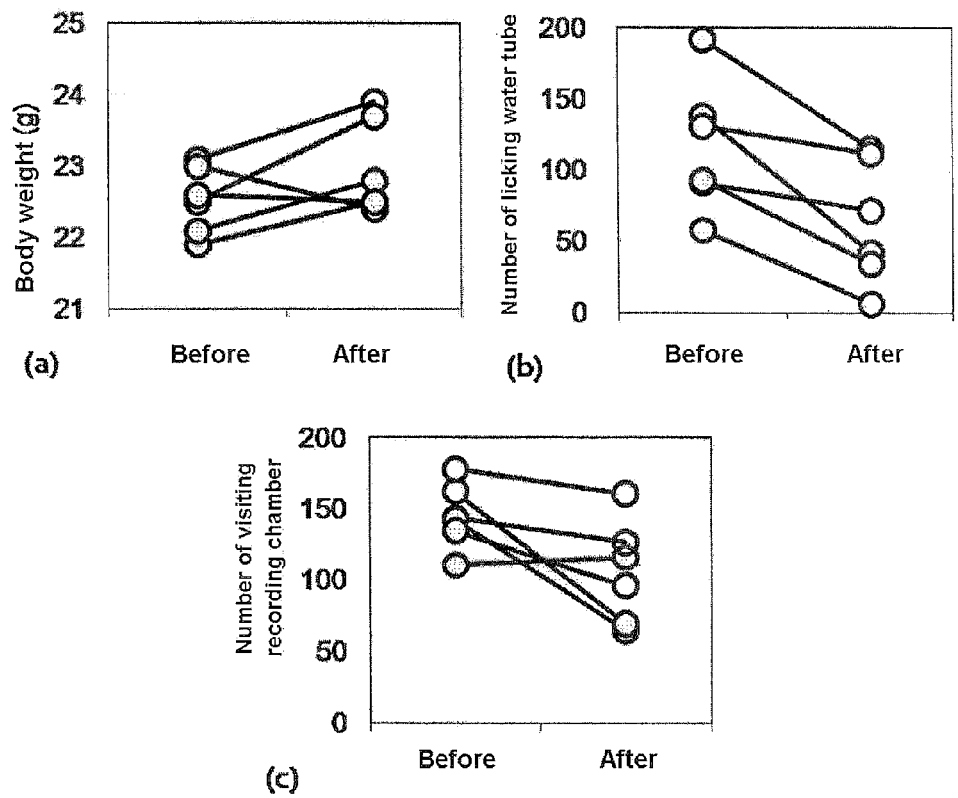

The blocks A, B and C denote a drug administration zone, a continuous spike wave zone and a spike-and-wave episode zone, respectively.);

FIG. 15 shows entropy of individual channels with the lapse of time (4-AP was administered at 10 minutes.);

FIG. 16 shows spatial distribution of entropy during a continuous spike wave episode, and FIG. 17 shows spatial distribution of entropy during an SWD episode (In FIGS. 16 and 17, the same color represents the same scale);

FIGS. 18 and 19 show phase shift for continuous spike waves (FIG. 18) and SWD (FIG. 19) ((+) phase indicates that the corresponding region leads in view of seizure travel, whereas (−) phase indicates that the corresponding region lags. The phase shift was determined from the subtraction of the means of the phases.); and FIG. 20 shows the change of mouse behaviors before and after the implantation of an EEG electrode ((a) shows the change of body weight of mouse (p-value=0.084, paired t-test), (b) shows the change of the number of licking a water tube (p-value=0.004, paired t-test), and (c) shows the change of the number of visiting a recording chamber (p-value=0.026, paired t-test). The mass of a connector and dental cement was excluded in the calculation of body weight.).

BEST MODE

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first", "second" and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

This disclosure provides a method for recording laboratory animal electroencephalography (EEG) capable of simultaneously recording EEG from as many sites as possible in a least invasive manner and in a most effective way, using a polyimide-based microelectrode. Since polyimide has superior biocompatibility, it may be micro fabricated into a flexible microelectrode by a photolithographic process. Compared with a hard silicon electrode, a polyimide microelectrode may reduce tissue damage because it is elastic and reduces incompatibility of the electrode with the tissue.

The laboratory animal may be a small animal such as rodents. In an embodiment, a mouse may be used.

In an embodiment, a polyimide-based microelectrode array for an EEG electrode, capable of recording up to 30 channels from a freely-moving laboratory animal, is designed. A micro-sized connector is attached to the microelectrode to enable an organ implantation of the electrode for a long-term recording of a subject. The weight of an electrode, including the connector, is 150 mg, and the total weight including dental cement for fixation does not exceed 300 mg. The electrode was implanted to a mouse and was compared with an existing screw electrode.

This disclosure provides a polyimide-based microelectrode for recording of laboratory animal EEG advantageous over the existing screw electrode. Since the polyimide microelectrode coupled with the connector is elastic and light, it may be easily applied to the skull of a small laboratory animal, without causing any behavioral disorders of the animal. No invasive procedure such as making holes is required. The implanted connector is connected to a signal acquiring apparatus, so that EEG may be recorded while the laboratory animal is freely moving. As a result, long-term study of EEG for laboratory animals including mice may be conducted easily. Another advantage of the polyimide microelectrode is that EEG may be acquired from a considerably larger number of channels than the existing method. According to an embodiment, 32 channels are used including two grounding electrodes. The number or arrangement of EEG channels may be varied depending on the purpose of study. Signals from individual channels are specific for the detection regions. However, the sensitivity is predetermined as a function of frequency, degree of synchronization and electrical properties in the brain. Processing of signals from the multi-channel EEG provides important information such as spatial and temporal distribution of entropy, coherence and phase shift. These statistical or dynamical variables may be employed to understand the spatial and temporal characteristics of the brain, with respect to connectivity, regularity and wave transportation. Considering the brain size of the small laboratory animal such as mouse, it may be possible to locate a power source deep in the brain and deliver a power from the source to the skull. As a result thereof, a functional EEG map for a freely moving laboratory animal will be able to be realized. If the microelectrode is coupled with a wireless transmitter, the laboratory animal EEG will become a more powerful tool.

MODE FOR INVENTION

The examples and experiments will now be described. The following examples and experiments are for illustrative purposes only and not intended to limit the scope of this disclosure.

Example

1. Design of Microelectrode

Electrodes for human electroencephalography (EEG) are usually located according to the 10-20 or 10-10 system recommended by the American EEG Society. The electrodes are uniformly positioned on two anatomical landmarks (the nasion and the inion) of the human scalp. Before positioning the electrodes, it is important to remove hair and apply a conductive gel between the electrode and the scalp to make the electrode characteristics uniform.

For mouse EEG, the electrode may be directly placed on the mouse skull after vertical incision of the scalp. However, the area of the exposed skull is limited. The infratemporal region of the skull is held by a network of muscle tissue transmitting a muscle signal. The surface of a mouse skull has landmarks such as the bregma (the point of meeting of the sagittal and coronal sutures) and the lambda. Traditionally, the bregma is used as a reference point. The distance between the bregma and the lambda increases with body weight. For grown mice (C57BL/J5) weighing 26-30 g, the average distance is 4.2 mm. The frontal region accessible to the flexible electrode is about 3 mm ahead of the bregma and about 2 mm lateral from the midline. For the vertex and temporal region, the area of about 4 mm lateral from the midline is accessible by the flexible electrode.

Electrodes having contacts of different size (316, 422, 562, 750, 1000 and 1334 μm in diameter) were tested prior to the arrangement of the electrodes. The signal-to-noise ratio (SNR) varies depending on the size of the electrical contact. Although signals from the brain are enhanced, the background noise also increased with the contact area. The SNRs for mouse θ (5-8 Hz) and α (9-12 Hz) rhythms are defined by the following equation.

$$SNR(\theta, \alpha) = 10\log\left(\frac{P(\theta, \alpha)}{P(60\ Hz)}\right)$$

Figure 1:
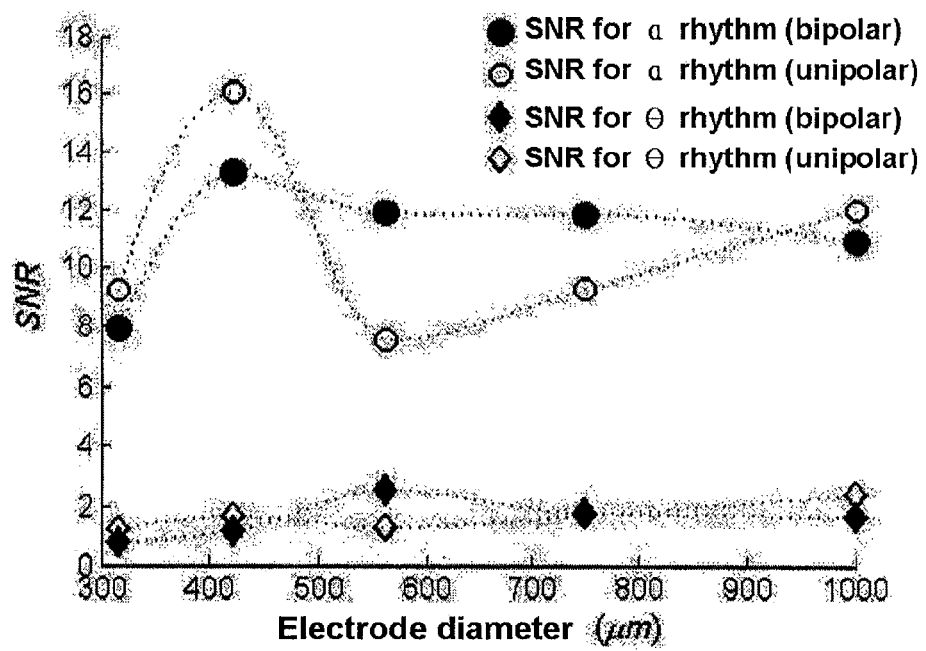
FIG. 1 shows signal-to-noise ratios (SNRs) at different size of electrical contacts of a polyimide-based microelectrode (The SNR was calculated for θ (5-8 Hz) and α (9-12 Hz) rhythms.)

In the equation, $P(\theta, \alpha)$ is a spectral density for θ and α rhythms, integrated over a frequency range of 5-8 Hz and 9-12 Hz, respectively. SNR values for θ and α rhythms were obtained for both bipolar and unipolar recording, and are presented in FIG. 1. FIG. 1 shows SNRs at electrical contacts with different size of a polyimide-based microelectrode. EEG was acquired by bipolar and unipolar recording from the mouse skull. SNRs were calculated for θ (5-8 Hz) and α (9-12 Hz) rhythms. The curves show that a relatively large SNR is attained with an electrode diameter of 400-500 μm. In spite of the point of the local maximum being poor, the curves indicate that an adequate contact area is attained with an electrode diameter of 400-500 μm. In an embodiment, the contact area may be 0.1-100 mm².

Figure 2:
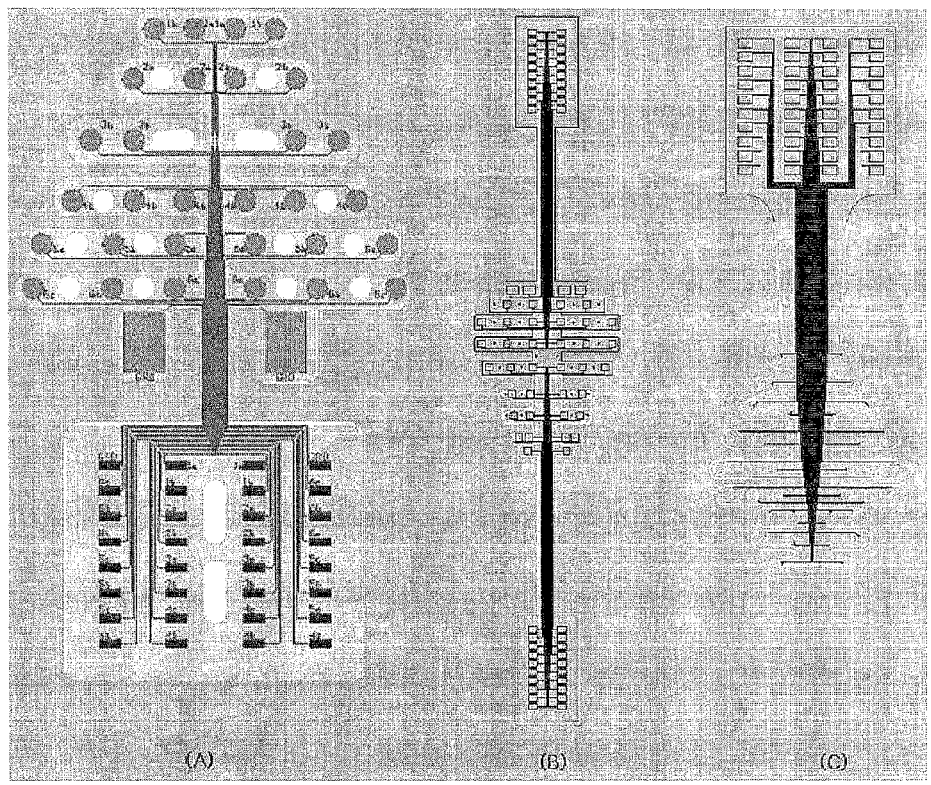
FIGS. 2-5 show a configuration of a mouse electroencephalography (EEG) microelectrode according to an embodiment (FIG. 2), a photograph of a manufactured electrode (FIG. 3), a photograph of a mouse skull after the electrode is set up (FIG. 4), and a photograph of a mouse head taken from the backside (FIG. 5)

Based on the preliminary test result, a flexible, multi-channel mouse EEG electrode was designed. FIG. 2 shows a configuration of a mouse EEG microelectrode according to an embodiment. It includes 30 symmetrically aligned recording electrode contacts (500 μm in diameter), and 2 grounding electrodes (1000×1500 μm²). The location of the recording electrodes are given in Table 1. Table 1 shows 3D Cartesian coordinates of the electrodes. The bregma was set as the origin. In the design of the 2D electrode, the horizontal dimension was determined by the root mean square of $x^2+z^2$, and y was used to set the vertical dimension.

TABLE 1

|  | 1A | 1B | 2A | 2B | 3A | 3B | 4A | 4B | 4C | 5A | 5B | 5C | 6A | 6B | 6C |
|---|---|---|---|---|---|---|---|---|---|---|---|---|---|---|---|
| x (mm), mediolateral | 0.50 | 1.50 | 0.50 | 2.00 | 2.00 | 3.00 | 0.75 | 2.00 | 3.25 | 1.00 | 2.50 | 4.00 | 1.00 | 2.50 | 4.00 |
| y (mm), anteroposterior | 2.26 | | 1.00 | | −0.51 | | −2.00 | | | −3.08 | | | −4.18 | | |
| z (mm), dorsoventral | −0.20 | −0.30 | −0.20 | −0.50 | −0.20 | −0.60 | 0.27 | 0.17 | −0.73 | 0.22 | −0.03 | −1.03 | 0.17 | −0.23 | −1.53 |

As seen in FIG. 2, in order to fix the electrode on the rough surface of the skull with no noncontact points and to enable easy positioning, the recording electrode contacts were aligned on a plurality of parallel arms extending from the centerline, like the veins of a leaf.

1-2. Manufacture of Microelectrode

Electrode contacts, connecting wires, and interconnect pads were formed by depositing platinum (Pt) to a thickness of 300 nm by sputtering on a 5 μm-thick polyimide substrate (Pyralin 2611, HD Microsystems, Bad Homburg, Germany) formed by spin coating. Besides Pt, most conductive materials such as Ag, AgCl, Au, AuCl, etc. may be deposited on the polyimide substrate.

After patterning a metal layer by a photolithographic process, a second polyimide layer with the same thickness was spin coated on the uppermost layer. Thereafter, the electrode contacts and interconnect pads were exposed by a selective reactive ion etching (RIE) of the polyimide layer. A connector (Omnetics Connector Corporation, Minn., USA) was attached to the interconnect pad using a conductive paste (silver paste). The microporous structure of Pt formed by the metal deposition increases the substantial surface area of the electrode, thereby reducing impedance at the interface. In an embodiment, the connector may be attached on the interconnect pad using an anisotropic conductive film (ACF). Two connectors each having 16 pins may be used as in FIG. 2 (A), or connectors as in FIG. 2 (B) or (C) may be used. Also, as in FIG. 2 (B), two connectors may be connected on both sides of the electrode.

Figure 3:
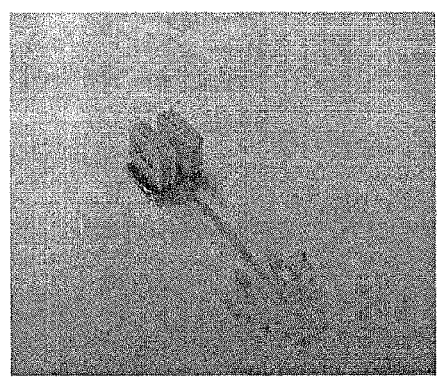

FIG. 3 is a photograph of the electrode along with the connector manufactured according to an embodiment. It is 10 μm thick, with a maximum width of 1 cm and a total length of 2.6 cm (The length of the portion actually contacting the skull is 9.3 mm.). In an embodiment, the thickness of the electrode may be 1-1000 μm.

Test Example 1

Analysis of Electrode Characteristics

Electrochemical characteristics of the electrode were analyzed using an impedance spectrometer before and after Pt deposition (measurement amplitude: 50 mV; frequency range: 10-10$^5$Hz). The measurement was made using a three electrode setup including a Pt counter electrode (PT 1800, Schott Instruments, Mainz, Germany) and an Ag/AgCl reference electrode (B 2920, Schott Instruments, Mainz, Germany). The setup was coupled with an electrochemical interface (1287, Solartron Analytical, Farnborough, UK) and a frequency response analyzer (1255, Solartron Analytical, Farnborough, UK). The measurement was made in a physiological saline solution (0.9%) at room temperature. In order to remove organic residues on the electrode surface and to stabilize the impedance measurement, the electrode was cycled between −0.6 V and +0.9 V (scan rate: 0.1 V/s) prior to the analysis.

<Result>

Figure 6:
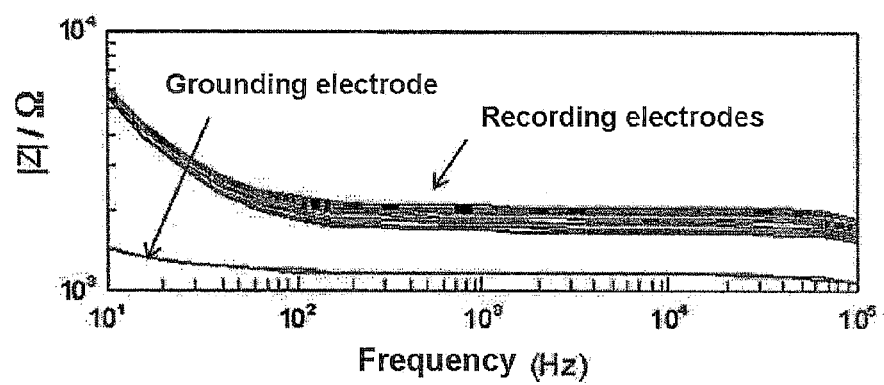
FIG. 6 shows absolute value of impedance |Z| (Ω)
Figure 7:
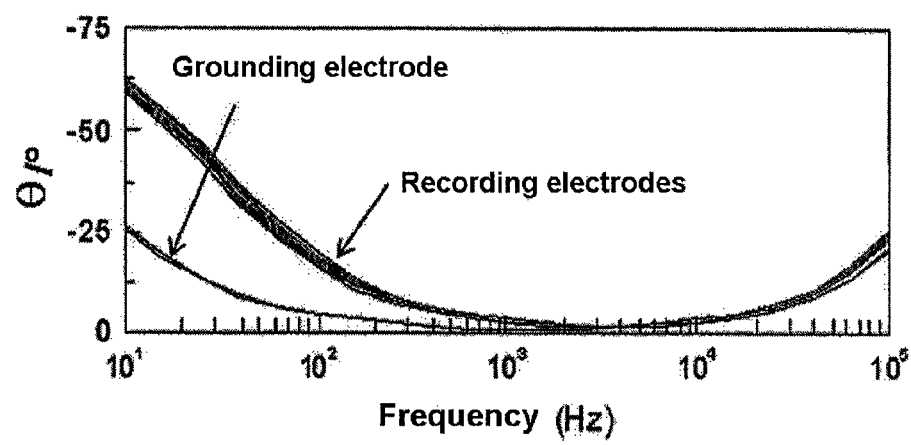
FIG. 7 shows phase shift θ (°, degree), at different measurement frequencies.

FIG. 6 shows absolute value of impedance |Z| (Ω) and FIG. 7 shows phase shift θ (°, degree), at different measurement frequencies for the packaged EEG electrode including 30 recording electrodes and 2 grounding electrodes. For the electrodes with the same size, the deviation of the absolute value of impedance and the phase shift is 7-20% and 5-40%, respectively. Within the EEG frequency range, the deviation of the absolute value of impedance increases as the frequency increases, whereas the deviation of the phase shift decreases. All the electrodes exhibited exponential increase of absolute value of impedance and phase shift as the frequency decreases, which is the characteristic behavior at the electrode-electrolyte interface.

Test Example 2

In Vivo Test

Mouse EEG was recorded in vivo using an electrode according to an embodiment of this disclosure.

2-1. Comparison of EEG Signals from Existing Screw Electrode and Microelectrode According to the Disclosure EEG signals from an existing screw electrode and a microelectrode according to an embodiment of this disclosure were compared at the same time. A mouse (8 weeks old, body weight 25 g) was anesthetized with Avertin (2% 20 μl/g, 20 mL/body weight kg) and placed on a stereotaxic apparatus (an apparatus used to examine the brain 3-dimensionally for brain surgery or study) (David Kopf Instruments, Model 902, Calif., USA). After incising an area of 2.0×2.5 cm with respect to the midline, the scalp was opened and fixed with a micro clamp. The skull was perforated and a screw electrode was implanted on the scalp (anteroposterior (AP): +2.5 mm, mediolateral (L): +2.5 mm). A pair of contacts of a microelectrode were positioned to be symmetric to each other with respect to the midline (AP: +2.5 mm, L: −2.5 mm). In order to generate a bipolar EEG biopotential, one screw electrode was positioned on the midline (AP: −1.75 mm, L: 0 mm). A grounding electrode was positioned on the cerebellum, 2 mm from the lambda point to the backside. In order to prevent the electrode from collecting background noise, spontaneously hardening glass ionomer (Vivaglass CEM, Ivoclar Vivadent, Germany) was cautiously coated on the electrode. In order to induce bilaterally synchronous spike-and-wave discharge (SWD), γ-butyrolactone (GBL, Sigma, Mo., USA) was intra-abdominally administered to the animal at a dose of 70 mg/kg. GBL is a prodrug of γ-hydroxybutyric acid (GHB) and is known to induce absence seizures.

<Result>

Figure 8:
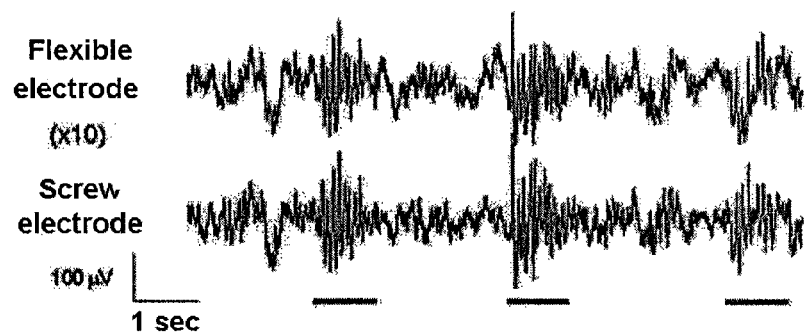
FIG. 8 shows mouse EEG after administration of γ-butyrolactone (GBL) (EEG signal from the flexible electrode was multiplied by 10. The horizontal bars indicate occurrence of spike-and-wave discharge (SWD) epilepsy.)

SWD was observed about 30 minutes after the administration of GBL. The measured SWD frequency was about 9-13 Hz for a duration of 1-5 seconds, with waxing and waning patterns. FIG. 8 shows sample tracing of mouse EEG after the administration of GBL from the screw electrode and the flexible electrode. SWD epileptic patterns were observed in both EEGs. The horizontal bars indicate occurrence of SWD epilepsy. EEG signals from the flexible electrode were multiplied by 10, because they were about 10 times smaller than those from the screw electrode under the same amplification setting. In order to evaluate the coherence of the EEGs from the two electrodes, a normalized coherence function, cohere (f), was calculated by the following definition.

$$\mathrm{cohere}(f) = \frac{|PSD_{xy}(f)|^2}{PSD_{xx}(f)PSD_{yy}(f)}$$

Figure 9:
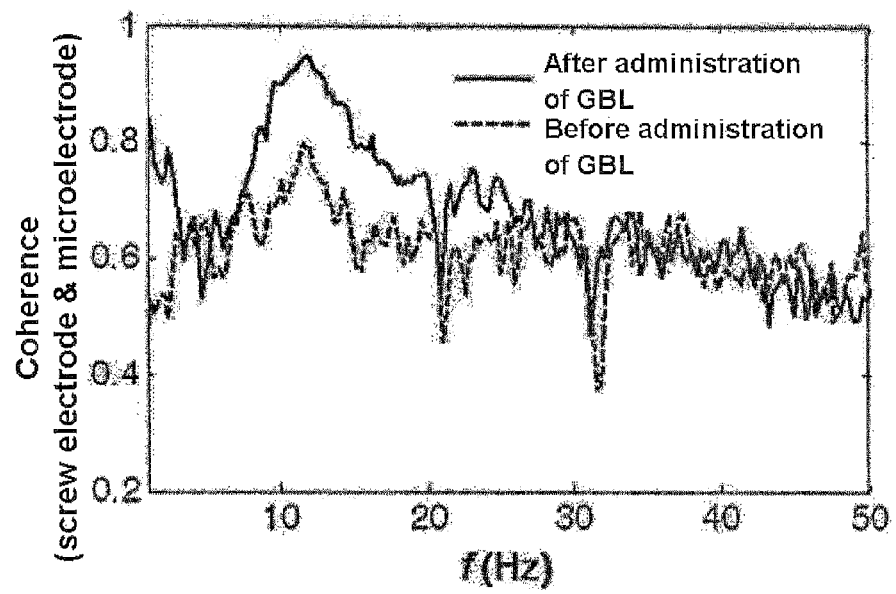
FIG. 9 shows coherence functions, cohere(f) of EEG signals from two types of electrodes (The broken and solid lines denote coherence functions before and after administration of GBL, respectively.)

In the equation, $PSD_{xy}(f)$ is a cross power spectral density of the two signals. The power spectral density describes how the power of a signal is distributed with frequency. The integral of the power spectral density function over all frequencies amounts to the mean square of signals in the time domain. FIG. 9 shows coherence functions cohere(f) of EEG signals from the two types of electrodes. The broken and solid lines denote coherence functions before and after the administration of GBL, respectively. A high coherence between the two SWD frequencies is observed after the administration of GBL.

Figure 10:
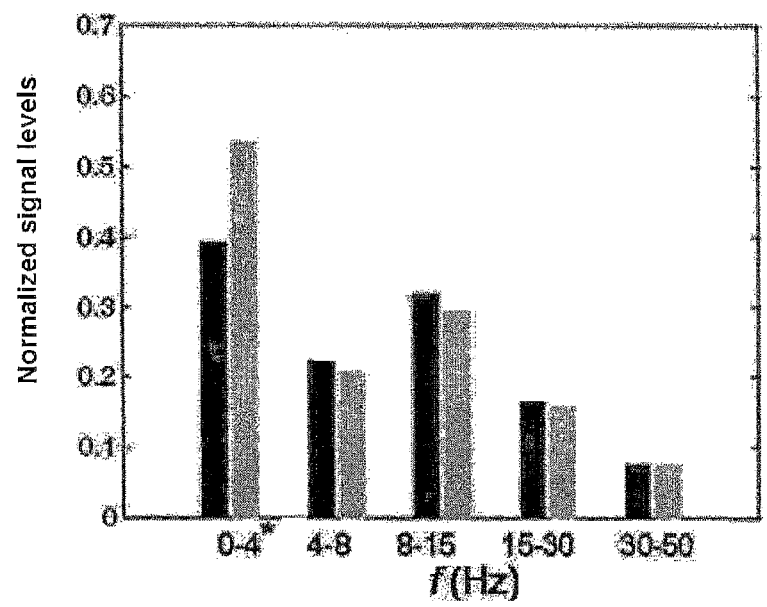
FIG. 10 shows signal levels in the EEG frequency region normalized to those of SWD (The black and gray bars denote normalized signal levels for a screw electrode and a flexible electrode, respectively.)

FIG. 10 shows signal levels in the EEG frequency region normalized to those of SWD. The black and gray bars denote normalized signal levels for the screw electrode and the flexible electrode, respectively. The normalized signal levels for individual EEG frequency regions are symmetrically filtered and defined as standard deviation for the corresponding frequencies. The amplitude of the SWD signals was used as normalizing factor. Except for the δ frequency region, no statistically significant difference was observed.

Cross correlations for the filtered EEG signals were calculated. $R^2$-values for δ, θ, α, β and γ frequency regions were 0.668, 0.821, 0.930, 0.847 and 0.757, respectively.

This result indicates that the frequency information is conserved well although the signal levels of the flexible electrode are 10 times smaller than those of the screw electrode in the supradural. A higher signal level of the flexible electrode in the low frequency region is because the signal amplitude is smaller than that of the screw electrode. In this regard, the noise 1/f of the electrode is larger in the normalized signal levels.

2-2. Simultaneous Recording from Multiple Regions of Mouse Skull Using Microelectrode A microelectrode according to an embodiment was applied to the skull of an acute seizure model mouse. For recording, 15 bipolar channels were defined as in Table 2. Table 2 shows combinations of electrode pairs for bipolar recording. The values obtained by subtracting $V_1$ from $V_2$ are amplified differential voltages. L and R stand for left and right hemispheres, respectively.

TABLE 2

| | Channel No. | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| $V_1$ | L-1A | L-1B | L-3A | L-3B | L-4A | L-5B | L-5C | L-6A | R-1A | R-1B | R-3A | R-3B | R-4A | R-5B | R-5C |
| $V_2$ | L-2A | L-2B | L-4B | L-4C | L-5A | L-6B | L-6C | R-6A | R-2A | R-2B | R-4B | R-4C | R-5A | R-6B | R-6C |

Figure 4:
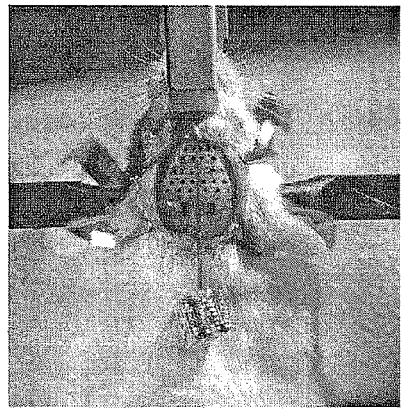
Figure 5:
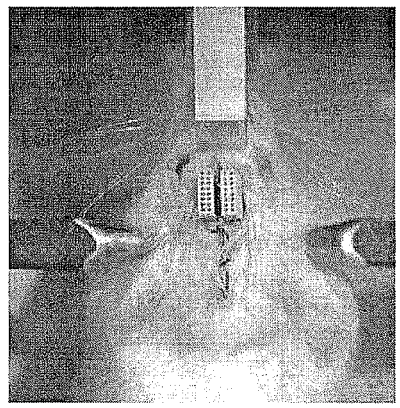

The animal (8 weeks old, body weight 25 g) was prepared in the same manner described above. A microelectrode was positioned on the skull and the remaining tissue was removed with a swab. The centerline of the electrode was aligned on the midline of the skull. The electrode was aligned so that the middle of the second and third lines of the microelectrode was positioned on the bregma. Before positioning the microelectrode, it is important to provide moisture to the skull using saline. In moist state, the microelectrode is naturally attached to the skull. FIG. 4 is a photograph of the mouse skull after the flexible electrode was set up. After the positioning, the electrode was fixed using a small amount of dental cement. FIG. 5 is a photograph of the mouse head taken from the backside after fixing with a connector. One hour after the administration of Avertin, 4-aminopyridine (4-AP, Sigma, Mo., USA) was intra-abdominally injected at a dose of 10 mg/kg to induce seizure. 4-AP, which blocks the nonspecific potassium channel, is commonly used to induce convulsive seizure.

The signals had a notch of 60 Hz and were recorded using a Grass 8-16C amplifier (Grass Technologies, R.I., USA), a band-pass filter for 0.3-70 Hz. The analog signals were digitized at a sampling frequency of 1 kHz using 16-bit Digidata 1440A (Molecular Device, USA).

Through simultaneous recording from multiple points on the mouse skull, the brain activities underlying region could be monitored in real time. A quantitative method was applied to the analysis of the multi-channel EEG signals. To describe the inter-channel relationships in the mouse EEG, Shannon entropy, coherence and phase methods were employed.

In information theory, the Shannon entropy is a measure of the decreased uncertainty of a receiver. The decreased uncertainty is quantified as a low entropy. In contrast, a high entropy is often associated with unpredictability. In some studies, the Shannon entropy was employed to analyze the dynamical behavior of EEG, for example, in patients with Alzheimer's disease or epilepsy. The Shannon entropy is defined as follows.

$$\text{Entropy} = -\frac{1}{N}\sum_{i=1}^{N} p\log_2 p_i$$

In the definition, $p_i$ is the distribution of the signal value of the i-th signal bin. The sum of all $p_i$'s is 1. N is the number of signal bins. In this test example, the Shannon entropy was measured every second and the change of entropy during the early and late seizure was compared with respect to the baseline.

The inter-channel relationship is an intrinsic characteristic that can be acquired form the multi-channel EEG. Such an interdependent variable is often measured through cross correlation. The cross correlation coefficient, or correlation, between signals from distant regions have been utilized for the evaluation of functional relationship during cognitive process or for the identification of seizure starting point. In this test example, the cross correlation coefficient $r_{n,m}$ of EEG signals from channels n and m was calculated as follows.

$$r_{n,m}^2(t) = \frac{\int_t^{t+1sec}(x_n(t')-\langle x_n(t')\rangle)(x_m(t')-\langle x_m(t')\rangle)dt'}{\sqrt{\int_t^{t+1sec}(x_n(t')-\langle x_n(t')\rangle)^2 dt' \int_t^{t+1sec}(x_m(t')-\langle x_m(t')\rangle)^2 dt'}}$$

In the equation, $x_n$ and $x_m$ are EEG signals from the channels n and m, respectively, and $\langle \rangle$ denotes the average.

The phase of a particular EEG pattern includes information on the speed of an oscillator for generating EEG oscillations or continuous spike waves. The phase of a Hilbert transformed EEG signal is often used to determine the phase of the signal in narrowband oscillations. For determining the rate of SWD for individual channels, the Hilbert transform was applied and phase angle was acquired immediately and compared with phase values of all the channels. A symmetric band-pass filter (10th order Butterworth, f=4.0-18 Hz) was applied prior to the Hilbert transform. The phase of discontinuous EEG signals such as continuous spikes or sharp waves may be acquired according to the method of obtaining an electrocardiogram (ECG) phase. A series of peak times $\{t_k\}$ may be allotted for all continuous spike waves or sharp waves. The phase at random time t is determined by linear interpolation of time shifts from the initial peak divided by the time interval between neighboring peaks.

$$\varphi(t) = 2\pi k + 2\pi \frac{t-t_k}{t_{k+1}-t_k}(t_k \leq t < t_{k+1})$$

Similarly to the phase angle of a continuous signal, the time derivative of the phase angle may be interpreted as the rate of the oscillator or frequency. The phase difference between different regions often reveals the relationship between the leading signal and the response signal over the whole range.

<Result>

Spatial and Temporal Analysis of Multi-Channel Mouse EEG

After administration of Avertin (2%, 20 μl/g, 20 mL/body weight kg) followed by systemic injection of 4-AP (10 mg/kg), brain activities were recorded using the microelectrode on the scalp. Spontaneous activation under anesthesia was observed from all initial locations.

Figure 11:
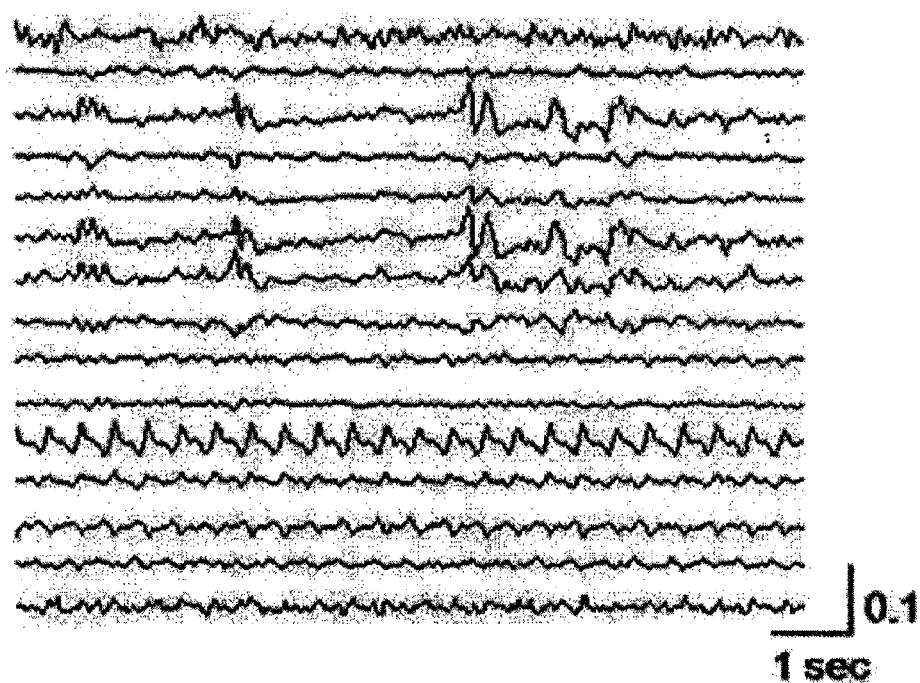
FIGS. 11-13 show bipolar EEG recorded with a polyimide-based microelectrode (The abscissa (x-axis) represents time and the ordinate (y-axis) represents voltage. Scales are shown at the right-bottom corner.
Figure 12:
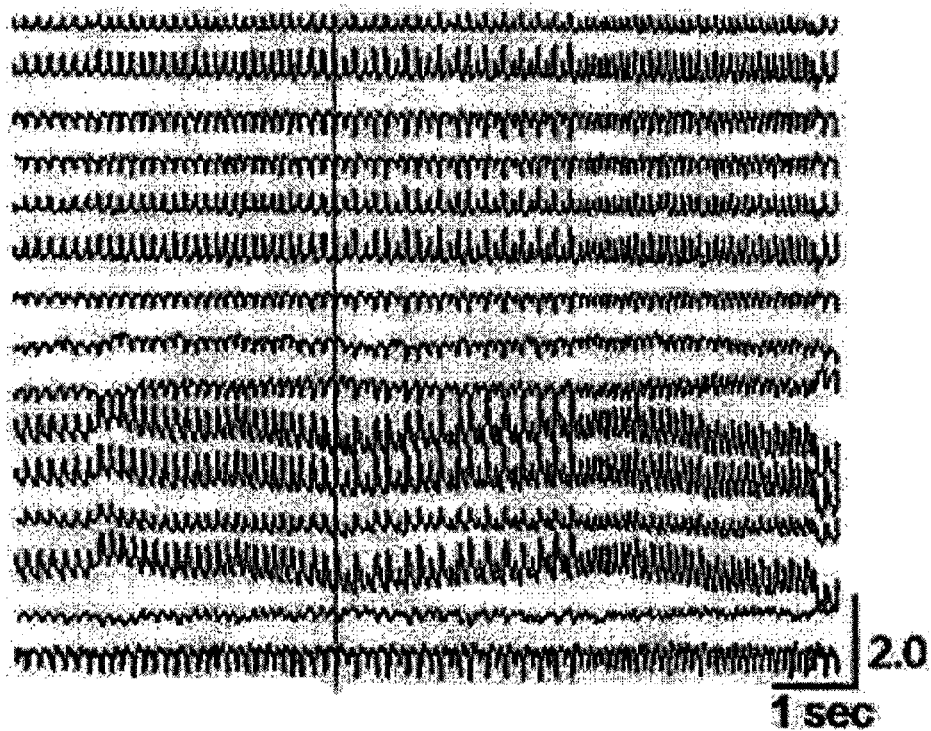
Figure 13:
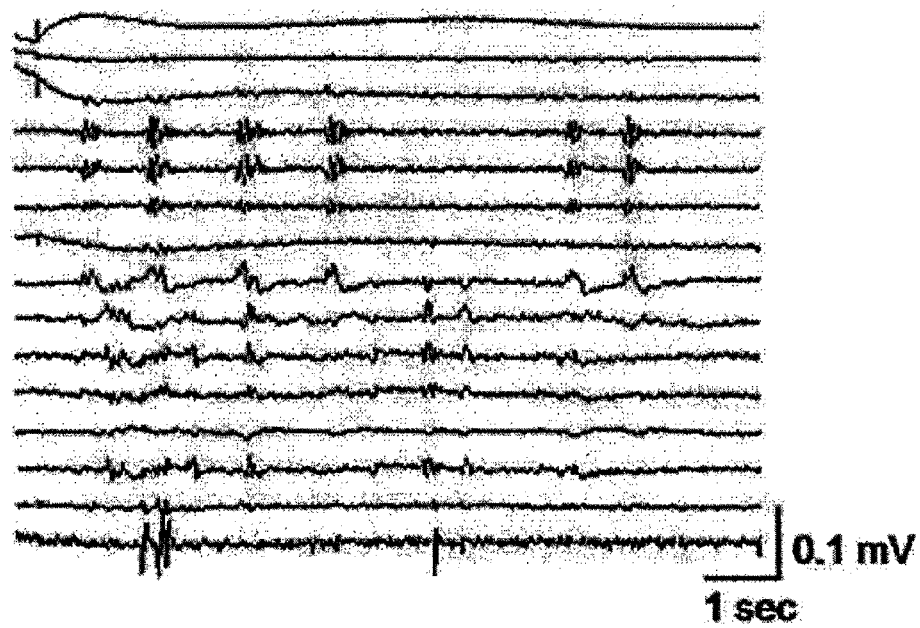

FIGS. 11-13 show bipolar EEG recorded with the polyimide-based microelectrode. The abscissa (x-axis) represents time and the ordinate (y-axis) represents voltage. Scales are shown at the right-bottom corner. FIG. 11 shows tracing of randomly selected EEG signals under Avertin anesthesia. In addition to the background wave, specific characteristics such as ripples are simultaneously observed in the individual regions. The dynamics of individual channels have relatively no coherence. FIG. 12 shows EEG exhibiting seizure waves 2 minutes after the administration of 4-AP. Continuous spike waves were generated following sporadic spikes with high amplitude. The continuous spike waves having the same amplitude and frequency were clearly observed from all the channels. Polarity, amplitude and speed of the brain waves were not the same in all the channels. The individual phase may be defined by the pattern of the spikes and the frequency of the continuous spike waves. The shift from one state to another is discontinuous. For example, the vertical broken line indicates a phase shift time from periodic to biperiodic. During such an episode, all the channels are highly synchronized. The phase shift occurred simultaneously in all the channels. The continuous spike waves lasted for about 2 or 3 minutes, and were repeated 2 times. A fast and broad oscillation of 30 Hz was observed between two spikes. FIG. 13 shows EEG exhibiting focal SWD (9 minutes after the administration). Such an SWD episode was first observed during the continuous spike wave episode, 6 minutes after the administration. With the SWD, the synchronous firing abruptly decreased. The speed of the spikes gradually decreased and the continuous spike waves disappeared. The SWD was first observed at channels 4 and 5, which corresponds to about 2-3 cm lateral from the midline and about 1 cm posterior from the bregma of the left hemisphere. The appearance of weak and focal SWDs became frequent and general with the passage of time. About 12 minutes after the administration, SWD was synchronously observed in all the channels.

Figure 14:
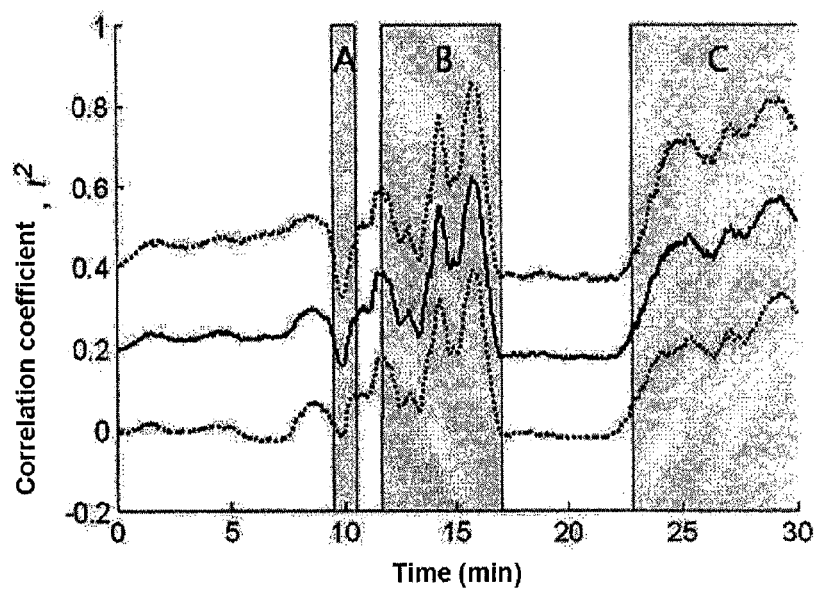
FIG. 14 shows cross-correlation coefficients (The solid line represents the mean of cross-correlation coefficients and the broken lines represent the range of standard deviation.

The inter-channel dependency was represented as cross correlation versus time. In FIG. 14, the solid line represents the mean of cross-correlation coefficients and the broken lines represent the range of standard deviation. The blocks A, B and C denote a drug administration zone, a continuous spike wave zone and a spike-and-wave episode zone, respectively. A high inter-channel dependency was observed during continuous spike waves (seizure waves) and overall SWDs. In general, a higher inter-channel dependency was monitored for a stronger epileptic signal.

The EEG entropy exhibited unpredictability in the distribution of EEG signals. FIG. 15 shows entropy of individual channels with the lapse of time. 4-AP was administered at 10 minutes. A high entropy was observed in the overall epileptic episodes. FIG. 16 shows spatial distribution of entropy during a continuous spike wave episode. The same time series as FIG. 12 were employed for calculation. FIG. 17 shows spatial distribution of entropy during an SWD episode. The same time series as FIG. 13 were employed for calculation. In FIGS. 16 and 17, the same color represents the same scale. As seen in FIGS. 16 and 17, a relatively high and nonuniform entropy was observed during the continuous spike wave episode in the left hemisphere, whereas a very high entropy was observed during the SWD episode in the right hemisphere. The high entropy during the seizure period is contradictory to the previous researches where ripple entropy was applied to seizure data. In the previous studies, the seizure period was characterized by a low entropy, which implied an ordered and simple dynamic characteristics of the seizure period.

The determination of the leader portion of a seizure is important in predicting the direction and focus of the seizure transport. In a mouse model, a simultaneous recording of multiple extracellular regions may be applied in vivo or in vitro to elucidate the mechanism under a specific type of seizure. FIG. 18 shows phase shift of epileptic waves for continuous spike waves and FIG. 19 shows phase shift of epileptic waves for SWD. For continuous spike waves, spikes were simultaneously induced in all the channels and high phase synchronization was observed as the lagging spikes were synchronously activated. However, the phase mapping of the spikes illustrated in FIG. 18 shows that fluctuation was monitored at the right posterolateral region. The fluctuation of phase values suggest that the corresponding region is not synchronized or a phase interrupter exists. In FIG. 19, the synchronized region is smaller than that of the continuous spike waves. A spatial nonuniformess is observed. Unless the exact point is detected at the commencement of a seizure, it is difficult to find out where the seizure was originated. However, (+) phase indicates that the corresponding region leads in view of seizure travel, and (−) phase indicates that the corresponding region lags. This is the intrinsic characteristic of the multi-channel EEG.

Test Example 3

Animal Behavior after Implantation

In order to quantify behavioral restriction caused by the implantation of the mouse EEG electrode, body weight, water consumption and physical activities were monitored every day after the surgery. For quantification of physical activities and vitality, IntelliCage (V2.2, NewBehavior AG, Zurich, Switzerland) was used. The system includes 4 recording chambers which fit into the corners of the cage and count access to the recording chamber by radio frequency transmission. Water consumption was measured using a lickometer. On the first day of customization, 4 weeks prior to the implantation of the EEG electrode, 6 female mice (C57BL/6J-129S4/SvJae) weighing 19-22 g and 7 weeks old were brought in the IntelliCage. All the mice were accustomed in the IntelliCage for 2 weeks. After the customization, a transponder for radio frequency transmission was subcutaneously injected at the back of each mouse. Such behavior variables as water tube licking and poking the corner of the cage were recorded wirelessly. The behavior variables were acquired for a week prior to the EEG electrode implantation. Following surgery, all the mice were returned to their original cage for recovery. One week later, behavior variables were recorded. The mice were monitored for a week like before the EEG electrode implantation. Body weight was measured every day for the whole period. 12 light hours and 12 dark hours were exactly provided for the mice. All the data were collected with an IC controller (NewBehavior AG, Zurich, Switzerland).

<Result>

FIG. 20 shows the change of mouse behaviors before and after the implantation of the EEG electrode. (a) shows the change of body weight of mouse (p-value=0.084, paired t-test), (b) shows the change of the number of licking a water tube (p-value=0.004, paired t-test), and (c) shows the change of the number of visiting a recording chamber (p-value=0.026, paired t-test). The mass of a connector and dental cement was excluded in the calculation of body weight.

No fatal disorders such as hobbling or atrophy were observed after the microelectrode was implanted and fixed on the mouse skull using dental cement. No body weight was observed. Rather, a statistically insignificant body weight was observed.

The number of water tube licking and visiting the corner of the IntelliCage decreased significantly following the implantation. This suggests that the electrode implanted on the skull might interrupt the animal's physical activities and vitality. No conclusion may be made with respect to whether the electrode affects the brain status, e.g. sleeping pattern or vulnerability to specific drugs, based on this result. However, the lessening of physical activities should be considered in an experimental paradigm where the physical activities are very important.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

The invention claimed is:

1. A multi-channel microelectrode for recording of laboratory animal electroencephalography (EEG) including:
    a single, unitary linear substrate configured to be positioned on a midline of a skull of a laboratory animal;
    a plurality of arms extending from the linear substrate, the plurality arms symmetrically arranged on both sides of the linear substrate; and
    recording electrodes and grounding electrodes, each comprising a contact, a connecting wire and an interconnect pad,
    wherein the contacts of the recording electrodes are aligned on the plurality of arms, and
    wherein the recording electrodes and the grounding electrodes are symmetrically arranged on both sides of the linear substrate.

2. The multi-channel microelectrode for recording of laboratory animal EEG according to claim 1, wherein the area of the contact of the recording electrode is 0.1-100 mm$^2$.

3. The multi-channel microelectrode for recording of laboratory animal EEG according to claim 1, wherein the microelectrode has a thickness of 1-1000 μm.

4. The multi-channel microelectrode for recording of laboratory animal EEG according to claim 1, wherein the microelectrode further includes a connector which connects the grounding electrodes and the recording electrodes to a signal acquiring apparatus.

5. The multi-channel microelectrode for recording of laboratory animal EEG according to claim 4, wherein the interconnect pad connects the connector to the grounding electrodes and the recording electrodes, and the connector is connected to the interconnect pad by a conductive paste or an anisotropic conductive film (ACF).

6. A method for recording of laboratory animal EEG using the multi-channel microelectrode for recording of laboratory animal EEG according to claim 1, the method comprising:
    positioning the multi-channel microelectrode on the skull of a laboratory animal; and
    acquiring broadband EEG signals from the skull of the laboratory animal using the multi-channel microelectrode.

7. The method for recording of laboratory animal EEG according to claim 6, wherein positioning the multi-channel microelectrode comprises contacting the recording electrodes with symmetrical regions of the skull of the laboratory animal.

8. The method for recording of laboratory animal EEG according to claim 6, further comprising, providing saline to the skull before the microelectrode is positioned on the skull of the laboratory animal.

* * * * *